United States Patent [19]
Bird et al.

[11] Patent Number: 5,942,657
[45] Date of Patent: Aug. 24, 1999

[54] CO-ORDINATED INHIBITION OF PLANT GENE EXPRESSION

[75] Inventors: Colin Roger Bird, Bracknell; Rupert George Fray, Lenton; Donald Grierson, Shepshed; Wolfgang Walter Schuch, Corwthorne; Graham Barron Seymour, Worthing; Gregory Alan Tucker, Shepshed, all of United Kingdom

[73] Assignee: Zeneca Limited, London, United Kingdom

[21] Appl. No.: 08/335,763

[22] PCT Filed: May 13, 1993

[86] PCT No.: PCT/GB93/00979

§ 371 Date: Jan. 9, 1995

§ 102(e) Date: Jan. 9, 1995

[87] PCT Pub. No.: WO93/23551

PCT Pub. Date: Nov. 25, 1993

[30] Foreign Application Priority Data

May 13, 1992 [GB] United Kingdom .................. 9210273

[51] Int. Cl.[6] .................. A01H 5/00; C12N 5/14; C12N 15/29; C12N 15/52; C12N 15/82
[52] U.S. Cl. .................. 800/205; 435/172.3; 435/320.1; 435/419; 536/23.2; 536/23.6; 800/DIG. 44
[58] Field of Search ................ 435/172.3, 240.4, 435/320.1, 419; 800/205, 250, DIG. 44; 536/23.2, 23.6

[56] References Cited

U.S. PATENT DOCUMENTS

| 5,283,184 | 2/1994 | Jorgenson et al. | 435/172.3 |
| 5,387,757 | 2/1995 | Bridges et al. | 800/205 |

FOREIGN PATENT DOCUMENTS 0455316  11/1991  European Pat. Off.

OTHER PUBLICATIONS

Walden et al. (Sep. 1995) Tibtech 13: 324–331.

Primary Examiner—Douglas W. Robinson
Assistant Examiner—Amy J. Nelson
Attorney, Agent, or Firm—Pillsbury Madison & Sutro LLP

[57] ABSTRACT

Process for the inhibition of two or more target genes which comprises introducing into the plant a single control gene which has distinct DNA regions homologous to each of the target genes and a promoter operative in plants adapted to transcribe from such distinct regions RNA that inhibits expression of each of the target genes. Constructs suitable for use in the process, as well as cells and plants containing such constructs are disclosed. Specific examples relate to the pectinesterse and polygalacturonase genes.

8 Claims, 5 Drawing Sheets

Orientation of cDNA fragments

Direction of transcription

CO-ORDINATED INHIBITION OF PLANT GENE EXPRESSION

This invention relates to novel DNA constructs, plant cells containing the constructs and plants derived therefrom. In particular it involves the use of recombinant DNA technology to control, and more specifically to inhibit, the expression of two or more genes in plants.

BACKGROUND OF THE INVENTION

Plant development is a complex physiological and biochemical process requiring the co-ordinated expression of many genes. The production of new plant varieties with improved agricultural or commercial qualities can be achieved by modifying this coordinated pattern of gene expression. Such modifications have been achieved by conventional plant breeding techniques. However, the exact changes in gene expression that result in the production of the improved variety have not been readily characterised. More recently, recombinant DNA techniques have been used to modify the expression patterns of individual, specific plant genes without directly affecting the expression of other plant genes. In this way, the expression pattern of an individual gene can be either enhanced or inhibited either in the whole plant or in specific tissues or developmental stages.

The inhibition of specific individual plant genes has been achieved by the introduction into the plant of novel genes designed to express RNA homologous, in part, to the endogenous plant gene. In several cases, it has been demonstrated that expression of the target gene can be inhibited by two different strategies. These involve the introduction of specific genes designed to express either antisense or sense RNA. A typical example is the down-regulation of the gene encoding the tomato fruit cell wall enzyme, polygalacturonase, by the expression of either antisense RNA (Smith et al 1988 Nature 344, 724–726) or sense RNA (Smith et al 1990 Mol Gen Genet 224, 477–481). A further example is the down-regulation of the gene encoding chalcone synthase in petunia by either sense or antisense RNA.

The mechanisms by which the expression of a specific gene is inhibited by either antisense or sense RNA genes are not clearly understood. It has been proposed that RNA-RNA duplex molecules may be formed within the cells resulting in the inhibition of expression. However, other and perhaps different mechanisms may operate for the two strategies for down-regulation. Specific individual genes have been inhibited by greater than 99% by the two strategies independently.

SUMMARY OF THE INVENTION

According to the present invention, we provide a process for the inhibition of two or more target genes which comprises introducing into the plant a single control gene which has distinct DNA regions homologous to each of the target genes and a promoter operative in plants adapted to transcribe from such distinct regions RNA that inhibits expression of the target genes. The distinct DNA regions homologous to each of the target genes may be either sense or antisense strands. This invention can be used to generate plants with the combined benefits of down-regulation of several individual genes or families of related genes.

The present invention further provides DNA constructs containing a plant promoter positioned to transcribe an RNA strand from at least two distinct DNA regions homologous to DNA from each of at least two target genes. The distinct DNA regions may be joined sequentially or separated by a spacer region (preferably relatively short) provided such spacer region does not contain a transcription stop signal. The RNA transcribed from this single gene will contain regions homologous to the RNA transcribed from the two or more target genes.

The present invention further comprises novel cells and plants adapted to carry out the process of the invention, or which (or ancestors of which) have been transformed with the constructs of the invention.

The use of DNA constructs according to the invention offers several advantages over alternative, more complex methods of generating plants expressing homologous RNA to two or more individual target genes:

1. Plants can be generated from a single round of transformation thereby eliminating the extra time and complexity of multiple rounds of transformation.
2. The use of a single gene will ensure that RNA homologous to the two or more target genes is transcribed at the same rate. Otherwise, multiple individual homologous genes located in a single construct may have different transcription rates in transformed plants.
3. The segregation patterns of a single, multiple-function gene in progeny of a transformed plant will be simpler than the segregation patterns of multiple, single-function genes that have been combined in the same plant, either by sexual crossing or multiple transformation. This will have significant benefits for subsequent plant breeding.

The genes to which the present invention can be applied include all plant genes for which there is an advantage in down-regulating their activity. In particular the invention can be applied to genes involved in fruit development or ripening-related processes of commercially important fruit-bearing plants, in particular tomato. These could involve combinations of any of the genes encoding: cell wall hydrolases (eg. polygalacturonase, pectin esterase, $\beta$-(1-4) glucanase (cellulase), $\beta$-galactanase ($\beta$-galactosidase)); ethylene biosynthetic enzymes (eg 1-aminocyclopropane-1-carboxylate synthase, ethylene-forming enzyme); carotenoid biosynthetic enzymes (eg prephytoene or phytoene synthase, phytoene desaturase). In addition to genes encoding known enzymes, other genes (eg those showing homology to: pTOM36, pTOM38, pTOM66, pTOM75, pTOM99, pTOM136) with ripening enhanced expression have been identified and may be used in combination with any of the other genes.

DNA constructs according to the invention preferably comprise a base sequence at least 10 bases in length for each of the unrelated target genes for transcription into RNA. There is no theoretical upper limit to the base sequence for each homologous sequence—it may be as long as the relevant mRNA produced by the cell—but for convenience it will generally be found suitable to use sequences between 100 and 1000 bases in length. There is no theoretical limit to the length of the region separating the homologous sequences. The preparation of such constructs is described in more detail below.

The preferred DNA for use in the present invention is DNA derived from CDNA or genomic DNA of the target genes. The required homologous DNA can be obtained in several ways: by cutting with restriction enzymes an appropriate sequence of such DNA; by synthesizing a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA fragments from each of the unrelated target genes is then either ligated together prior to cloning or cloned sequentially into a vector containing upstream promoter and downstream terminator sequences.

Recombinant DNA and vectors according to the present invention may be made as follows. Suitable vectors containing the desired base sequences for transcription are treated with restriction enzymes to cut the sequences out. The DNA strands so obtained are cloned either simultaneously or sequentially into a second vector containing the desired promoter sequence (for example cauliflower mosaic virus 35S RNA promoter or the tomato polygalacturonase gene promoter sequence—Bird et al., Plant Molecular Biology, 11, 651–662, 1988) and the desired terminator sequence (for example the 3' of the Agrobacterium tumefaciens nopaline synthase gene, the nos 3' end).

According to the invention we propose to use both constitutive promoters (such as cauliflower mosaic virus 35S RNA) and inducible or developmentally regulated promoters (such as the ripe-fruit-specific polygalacturonase promoter) as circumstances require. Use of a constitutive promoter will tend to affect functions in all parts of the plant: while by using a tissue specific promoter, functions may be controlled more selectively. Thus in applying the invention, e.g. to tomatoes, it may be found convenient to use the promoter of the PG gene (Bird et al, 1988, cited above). Use of this promoter, at least in tomatoes, has the advantage that the production of homologous RNA is under the control of a ripening-specific promoter. Thus the homologous RNA is only produced in the organ in which its action is required. Other ripening-specific promoters that could be used include the E8 promoter (Diekman & Fischer, 1988 cited above).

Vectors according to the invention may be used to transform plants as desired, to make plants according to the invention. Dicotyledonous plants, such as tomato and melon, may be transformed by Agrobacterium Ti plasaid technology, for example as described by Bevan (1984) Nucleic Acid Research, 12, 8711–8721. The process may also be adapted for use with other techniques for generating transgenic plants. Such transformed plants may be reproduced sexually, or by cell or tissue culture.

The degree of production of homologous RNA in the plant cells can be controlled by suitable choice of promoter sequences, or by selecting the number of copies, or the site of integration, of the DNA sequences according to the invention that are introduced into the plant genome. In this way it may be possible to modify expression of the target genes to a greater or lesser extent.

The constructs of our invention may be used to transform cells of both monocotyledonous and dicotyledonous plants in various ways known to the art. In many cases such plant cells (particularly when they are cells of dicotyledonous plants).may be cultured to regenerate whole plants which subsequently reproduce to give successive generations of genetically modified plants. Examples of genetically modified plants according to the present invention include, as well as tomatoes, fruiting plants such as mangoes, peaches, apples, pears, strawberries, bananas and melons.

The specific embodiment of the invention that we have so far studied most thoroughly is the inhibition of both polygalacturonase and pectin esterase in ripening tomatoes. Modified tomato plants have been produced which contain a novel gene designed to express RNA with regions individually homologous to the tomato PG and PE genes. Fruit from some of the primary transformants have significant reductions of both PG and PE activity in the ripening fruit. This reduced enzyme activity is stably inherited as a single gene in progeny of the primary transformants. Plants such as these exhibit the combined benefits of reduced PG and PE activity and will be useful in the production of tomatoes with improved quality for fresh market and processed fruit.

DETAILED DESCRIPTION OF THE INVENTION

EXAMPLE 1

Construction of Combined PG-PE Sense Gene

A PG-PE sense gene was constructed by cloning bases 19 to 263 of the PG cDNA (pTOM6—Grierson et al 1986 Nuc. Acids Res. 14, 8595–8603) and bases 345 to 1665 of the PE cDNA (pPE1—Ray et al 1988 Eur. J. Biochem 174, 119–124) into the multiple cloning site of the vector pDH51. pDH51 is a pUC based vector which contains a multiple cloning site between the CaMV 35S promoter sequence and the CaMV 3' polyadenylation sequence. The orientation of the PG and PE sequences was determined by restriction mapping and DNA sequence determination of the borders of the inserted fragments. After verification of the structure of the vector, the expression module was isolated by digestion with pvuII and transferred to the plant transformation vector Bin19 (Bevan 1984 Nuc. Acids Res. 12, 8711–8721) to give the vector pPGPE (also known as pSB1).

EXAMPLE 2

Construction of Combined PG-PE Antisense Gene

Figure 1:
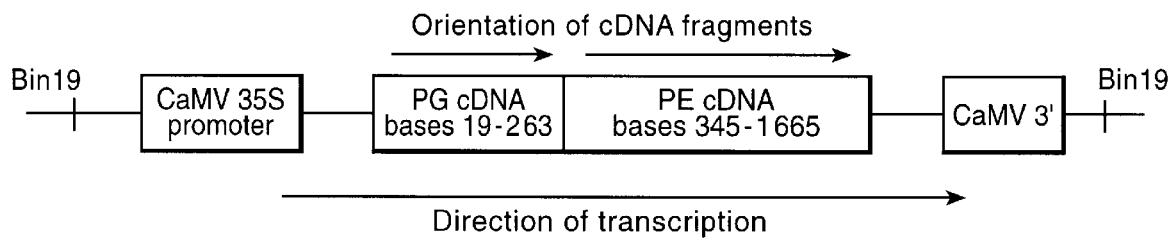
FIG. 1 shows the structure of the PG-PE sense gene in pPGPE.
Figure 2A:
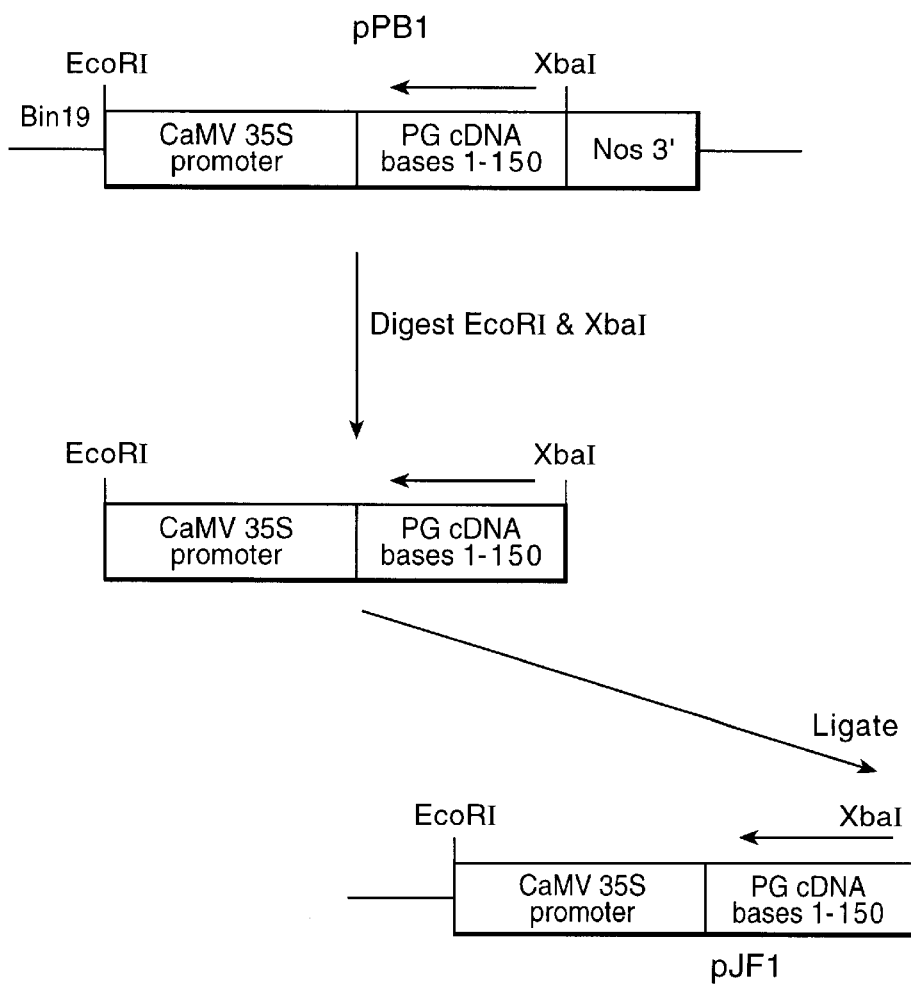
FIGS. 2A–2B present a diagram of the strategy for construction of the PG-PE antisense gene in pJF1.
Figure 2B:
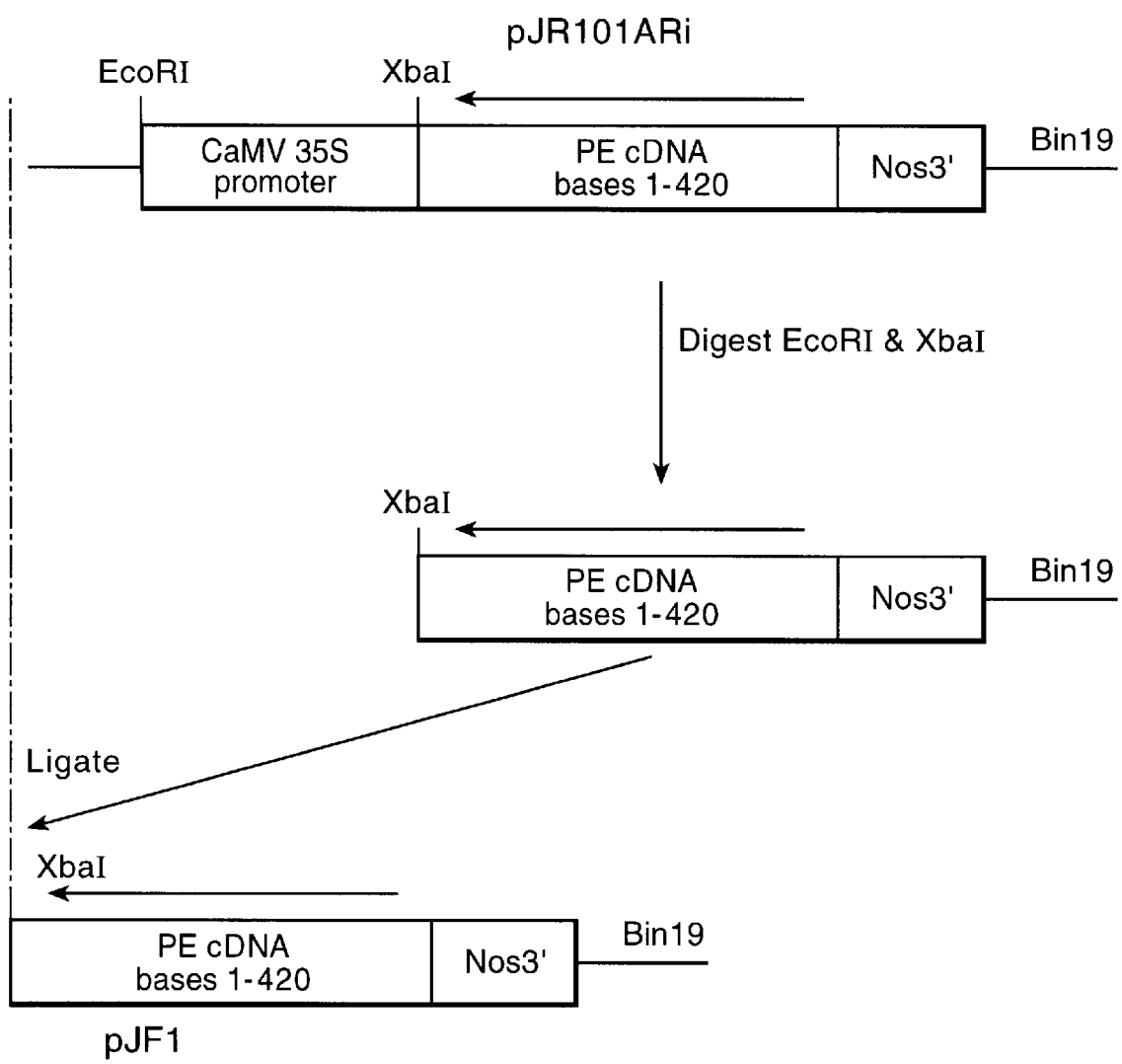

A PG-PE antisense vector (PJF1) was constructed as shown in FIGS. 2A and 2B. A 686 bp EcoRI-XbaI fragment from pPBI that contained the CaMV 35S promoter sequence and the first 150 bases from the 5' end of the PG cDNA (pTOM6) was isolated. The fragment was cloned into the EcoRI-XbaI sites of the PE antisense vector pJR101ARi after removal of the CaMV 35S promoter sequence. The construction of the vector was confirmed by PCR and DNA sequence analysis.

EXAMPLE 3

Generation of Transformed Tomato Plants

Vectors from Example 1 were transferred to *Agrobacterium tumefaciens* LBA4404 (a micro-organism widely available to plant biotechnologists) and were used to transform tomato plants. Transformation of tomato stem segments followed standard protocols (e.g. Bird et al Plant Molecular Biology 11, 651–662, 1988). Transformed plants were identified by their ability to grow on media containing the antibiotic kanamycin. Plants were regenerated, grown to maturity and the presence of the PG-PE sense gene was confirmed by genomic Southern analysis.

EXAMPLE 4

Analysis of Fruit from Transformed Plants

Figure 3A:
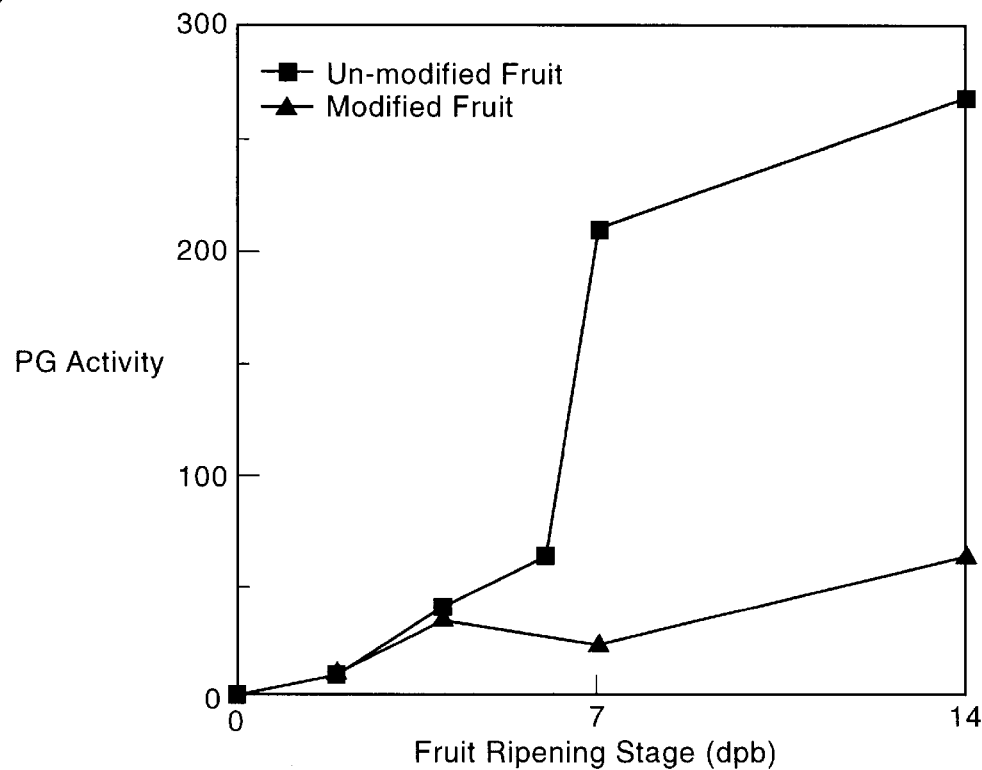
FIGS. 3A–3B are graphs of PG and PE activities in fruit from a tomato plant transformed with pPGPE ("dpb"="days post breaker")
Figure 3B:
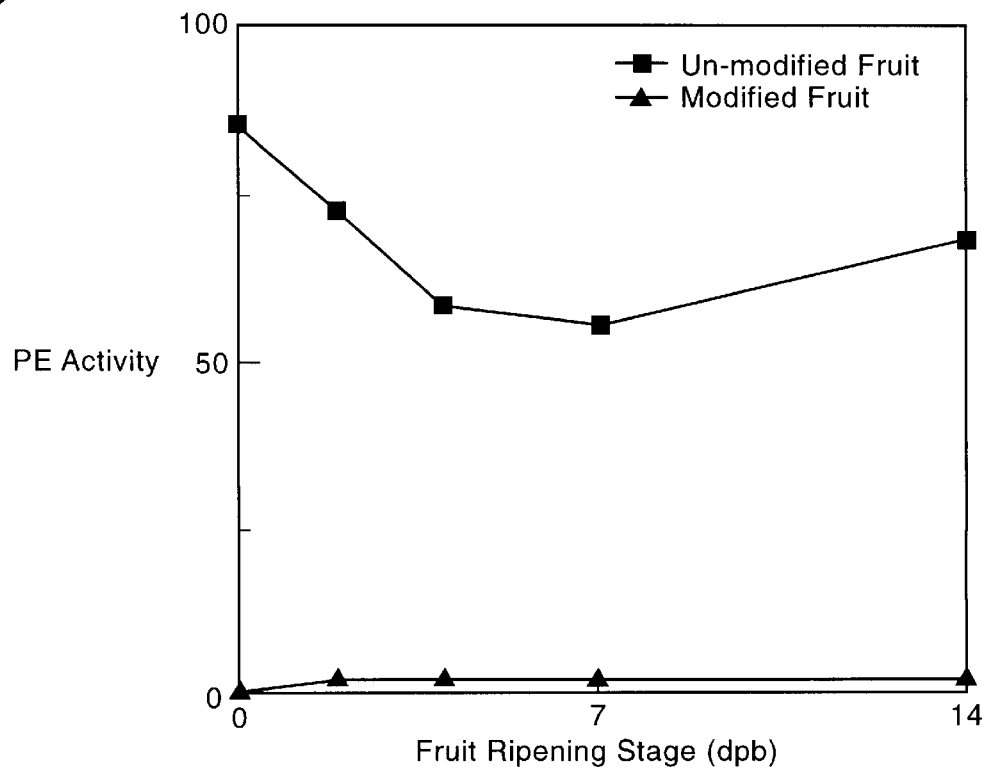

The PG and PE activities were assayed in ripening fruit from 3 plants transformed with pPGPE and several un-modified plants. The PG and PE activity was reduced by various extents in the fruit from all three transformed plants. The results for fruit from one of the transformed plants are shown in FIGS. 3A and 3B.

EXAMPLE 5

Analysis of Progeny of Transformed Plants

Self-fertilised seed from the pPGPE-transformed plant with the greatest reductions in PG and PE activities were germinated in the presence of kanamycin. Plants that were resistant to kanamycin were grown to maturity and enzyme activities in the fruit were analysed. These plants also had reduced PG and PE activity. Thus, the inheritance of the reduced PG and PE phenotype was confirmed.

EXAMPLE 6

Figure 4:
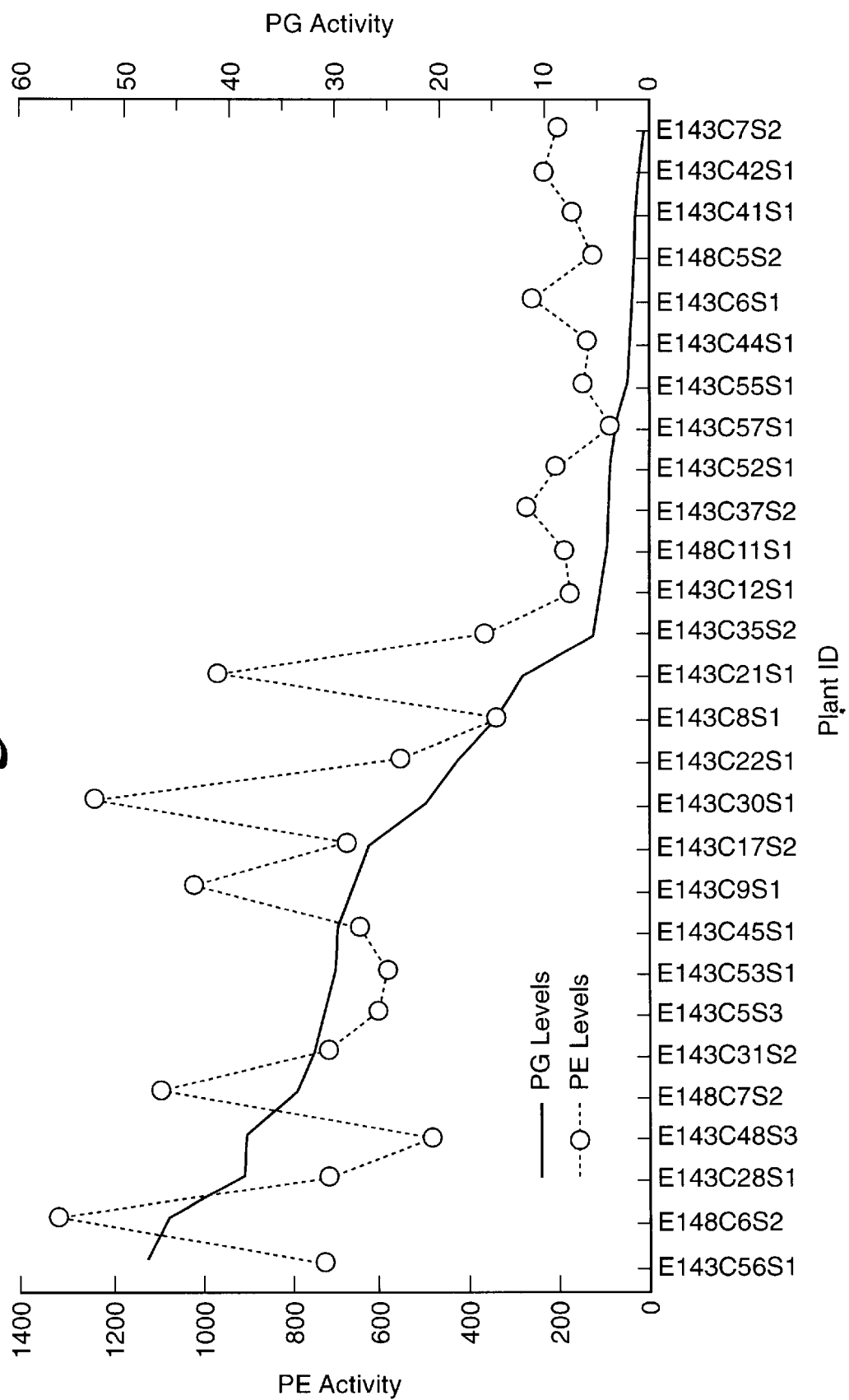
FIG. 4 shows PG and PE activity in fruit from 28 tomato plants transformed with a PE-PG sense construct.

The sense construct pSB1 prepared in Example 1 was used to transform tomatoes of the variety UC82B, using the same protocol as in Example 3. Transformants were grown in the glasshouse. PG and PE enzyme activities were assayed in ripe fruit. Fruit from the first 28 plants to mature were analysed. The results are presented graphically in FIG. 4, ranked in order of decreasing PG level. These results confirm that plants with substantial reductions in both PG and PE activity were obtained from the population of transformants. In all plants with significantly reduced activity of one enzyme, the other was also reduced. Thus the sense down-regulation of the two genes was tightly linked.

EXAMPLE 7

Expression of Genes in Plants Containing Sense Constructs

Selfed progeny were grown from two primary transformants obtained from Example 3 with single sites of insertion (E148C11-PG expression 10% that of normal fruit, PE expression 20% normal: E143C44-PG expression 5% normal, PE expression 16% normal). Stable inheritance of the double sense gene was confirmed by genomic Southern analysis. Homozygous and azygous progeny were identified. Assays of ripe fruit PG and PE activities confirmed that the low PG and PE phenotype segregated with the sense gene:

|            |            | PG activity | PE activity |
|------------|------------|-------------|-------------|
| E143C44.16 | Homozygous | 1           | 108         |
| E143C44.30 | Azygous    | 34          | 307         |
| E148C11.1  | Homozygous | 2.5         | 98          |
| E148C11.25 | Azygous    | 34          | 480         |

(all nmol/hr/µg protein)

EXAMPLE 8

Expression of Genes in Plants Containing Antisense Constructs

Figure 5:
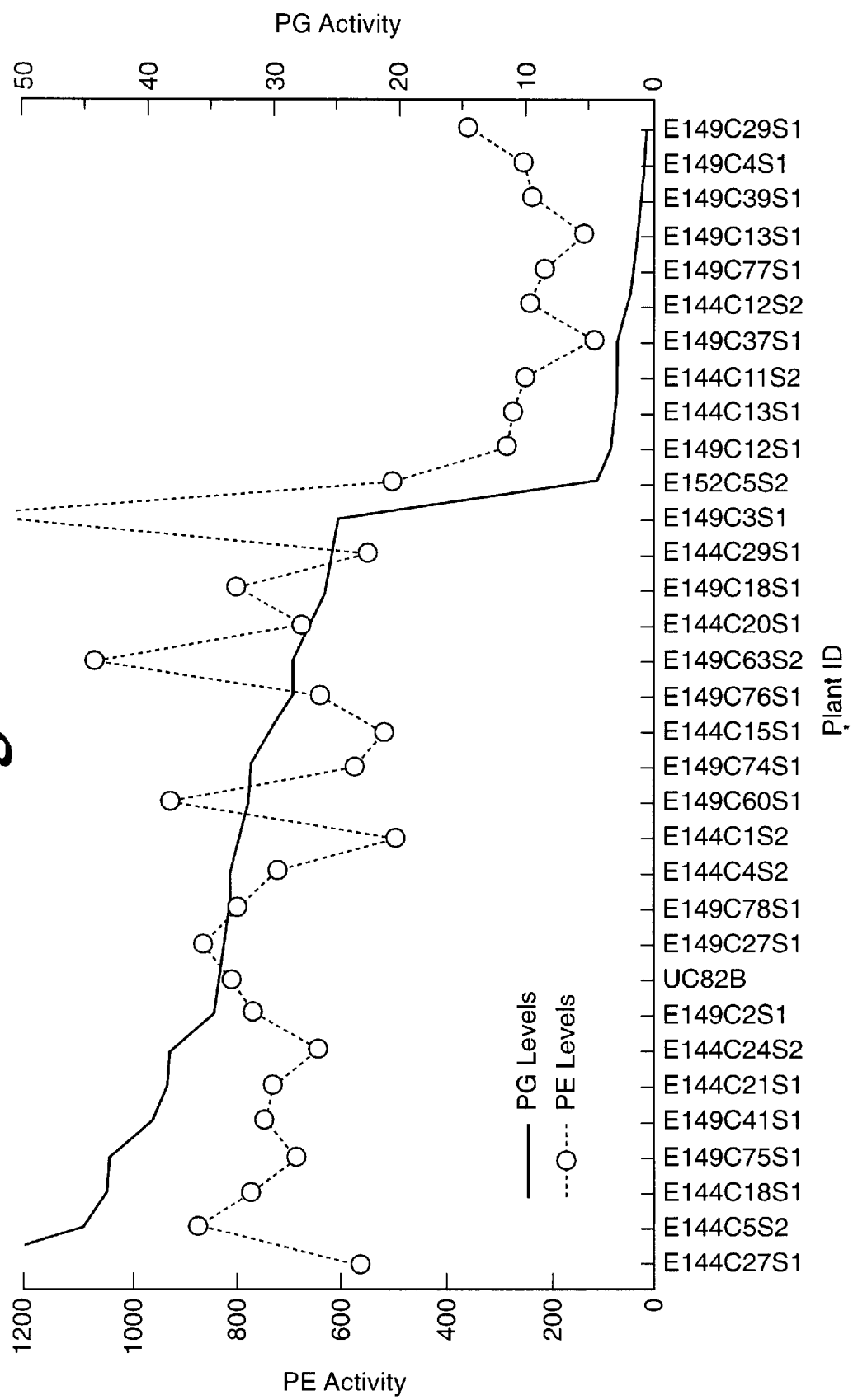
FIG. 5 shows PG and PE activity in fruit from 32 tomato plants transformed with a PE-PG antisense construct.

68 Transformants with pJF1 (from Example 2) in were generated in the tomato variety UC82B. PG and PE enzyme activities were assayed in ripe fruit. Fruit from the first 32 plants to mature were analysed. Untransformed UC62B is included as a control. The results are presented graphically in FIG. 5, ranked in order of decreasing PG level. As with the sense plants, reduced activities of the two enzymes were tightly linked.

This data confirms the utility of the antisense construct pJF1 (Example 2).

Analysis of selfed progeny confirms that both the antisense gene and the reduced PG/PE phenotype are inherited.

We claim:

1. A process for the inhibition of polygalacturonase and pectin esterase in a tomato plant which comprise introducing into the plant a single control gene which has distinct DNA regions homologous to the tomato polygalacturonase and tomato pectin esterase genes and a promoter operative in tomato plants adapted to transcribe from such distinct regions RNA that inhibits expression of each of the polygalacturonase and pectin esterase genes and allowing the thus transformed plant to grow, the DNA region homologous to the tomato polygalacturonase gene comprising at least a 100 base sequence of the pTOM6 gene and the DNA region homologous to the tomato pectin esterase gene comprising at least a 100 base sequence of the pPE1 gene.

2. A process as claimed in claim 1 in which at least one of the DNA regions is adapted to produce sense RNA.

3. A process as claimed in claim 1 in which at least one of the DNA regions is adapted to produce antisense RNA.

4. A process as claimed in claim 1 in which the promoter is a constitutive promoter.

5. A process as claimed in claim 1 in which the promoter is an inducible promoter.

6. A DNA construct comprising a single control gene which has distinct DNA regions homologous to the tomato polygalacturonase and tomato pectin esterase genes and a plant promoter positioned to transcribe an RNA strand from said two distinct DNA regions to inhibit expression of each of said genes, the DNA region homologous to the tomato polygalacturonase gene comprising at least a 100 base sequence of the pTOM6 gene and the DNA region homologous to the tomato pectin esterase gene comprising at least a 100 base sequence of the pPE1 gene.

7. A DNA construct as claimed in claim 6 in which at least one of the DNA regions is adapted to produce sense RNA.

8. A DNA construct is claimed in claim 6 in which at least one of the DNA regions is adapted to produce antisense RNA.

* * * * *